United States Patent [19]

Nukina et al.

[11] Patent Number: 4,540,666
[45] Date of Patent: Sep. 10, 1985

[54] METHANE FERMENTATION

[75] Inventors: Yasuyuki Nukina, Sennan; Syunji Namikawa, Minou; Toshikazu Tomioka, Ibaragi; Takehiko Yamamoto, Izumi; Susumu Oi, Suita, all of Japan

[73] Assignee: Matsushita Electric Industrial Company, Limited, Japan

[21] Appl. No.: 407,273

[22] Filed: Aug. 10, 1982

[30] Foreign Application Priority Data

| Aug. 13, 1981 [JP] | Japan | 56-127604 |
| Aug. 13, 1981 [JP] | Japan | 56-127606 |
| Aug. 13, 1981 [JP] | Japan | 56-127607 |

[51] Int. Cl.$^3$ .................. C12P 39/00; C12P 5/00; C12P 5/02; C12N 1/20; C12R 1/01; C12R 1/145

[52] U.S. Cl. .................. 435/167; 435/42; 435/166; 435/253; 435/822; 435/842

[58] Field of Search .............. 435/42, 166, 167, 289, 435/801, 813, 822, 842, 253; 210/603; 48/197 A

[56] References Cited

U.S. PATENT DOCUMENTS

| 3,880,717 | 4/1975 | Rubin et al. | 435/822 |
| 3,964,971 | 6/1976 | Johan et al. | 435/42 |
| 4,022,665 | 5/1977 | Ghosh et al. | 435/822 |
| 4,316,961 | 2/1982 | Klass et al. | 435/167 |
| 4,321,141 | 3/1982 | Messing | 435/176 |
| 4,323,367 | 4/1982 | Ghosh | 435/167 |
| 4,329,428 | 5/1982 | Ghosh et al. | 435/801 |
| 4,391,887 | 7/1983 | Baumgarten et al. | 435/42 |
| 4,396,402 | 8/1983 | Ghosh | 435/167 |

FOREIGN PATENT DOCUMENTS 3102739 11/1982 Fed. Rep. of Germany ...... 435/167

OTHER PUBLICATIONS

Bergey's Manual of Determining Bacteriology, (8th Ed.), pp. 474–476 and 557, 1974.
McKinney, R. E., *Microbiology for Sanitary Engineers*, McGraw-Hill, New York, pp. 247–253 (1962).
Doelle, H. W., *Bacterial Metabolism*, Academic Press, New York, pp. 115–127 (1969).

*Primary Examiner*—Thomas G. Wiseman
*Assistant Examiner*—Jayme A. Huleatt
*Attorney, Agent, or Firm*—Lowe, King, Price & Becker

[57] ABSTRACT

A methane fermentation process wherein a strain of the genus Methanobacterium is cultivated in a fermenter containing at least a carbon source, a nitrogen source, inorganic salts and micro-flora for methane fermentation. The strain has a methanogenic activity above $8.7 \times 10^{-8}$ ml/cell.day in the stationary phase of growth, exhibits the methanogenic activity even at an oxygen partial pressure of 1/30 atm. and is allowed to live under an oxygen partial pressure up to 1/5 atm. The seed of the strain is obtained by anaerobically cultivating the strain in a culture medium containing at least nitrogen sources, inorganic salts and reducing agents in a mesophilic range of 25° to 45° C. using a substrate such as a mixed gas of hydrogen and carbon dioxide, a formate or an acetate. The growth of the strain is facilitated when cocultured with a strain belonging to the genus Clostridium.

10 Claims, No Drawings

METHANE FERMENTATION

BACKGROUND OF THE INVENTION

1. Field of the Invention

This invention relates to a methane fermentation making use of novel methanogenic bacteria which exhibit high methanogenic efficiency and are highly resistant to oxygen.

2. Description of the Prior Art

A number of processes have been known for the production of methane gas by fermentation. Typical of high speed methane fermentation processes is a process which is described, for example, in the Collection of Prearranged Manuscripts of the Agricultural Chemical Society of Japan, p. 82, 1981. In this process the continuous fermentation operation is effected using a 0.5 $m^3$ liquefaction tank and a 1.5 $m^3$ gasification tank under conditions of a total retention time of 8 days and an organics labor of 15 kg/$m^3$· day thereby obtaining 300 l of a fermentation gas per kg of the organics having a methane concentration of 70% by volume. In this instance, the temperature conditions of thermophilic range (60° C.) where the high fermentation efficiency is achieved are adopted. The quantity of methane gas generated is 6.3 $m^3$/day and the retention times required for the gasification and liquefaction are, respectively, 6 and 2 days. The methane gas formation process in the gasification tank is the rate-limiting step of the whole fermentation process. In other words, in order to enhance the fermentation efficiency, the methane formation process in which methanogenic bacteria take part should proceed at high efficiency. Accordingly, the methanogenic activity of the bacteria is one of the most important factors controlling the efficiency of the whole fermentation process.

The above instance is a continuous fermentation process in which the concentration of the methanogenic bacteria in the gasification tank is held constant during the course of the stationary operation. In the continuous process, a given amount of fresh substrate is fed while withdrawing the same amount of the reactor effluent from the tank, so that methanogenic bacteria increase in an amount corresponding to that of bacteria entrained with the discharged effluent. Accordingly, when the doubling time of methanogenic bacteria is calculated from the charge and discharge rates of fermentation liquor, it is about 100 hours. That is, the increase or multiplication of methanogenic bacteria in the fermentation process is slight in degree, revealing that the methanogenic activity in the stationary phase of growth of methanogenic bacteria is very important for the methane fermentation.

As is clearly described in the Bergey's Manual of Determinative Bacteriology, methanogenic bacteria are very strict anaerobes and will die out within a short time when oxygen is incorporated into the system even in very small amounts. This characteristic of high sensitivity and low resistance to oxygen involves a considerable difficulty in case where the seed of methanogenic bacteria is preserved, subjected to the mass culture and/or transported. Accordingly, methanogenic bacteria to be used in practical applications should desirably be highly resistant to oxygen.

SUMMARY OF THE INVENTION

It is therefore an object of the present invention to provide a methane fermentation process in which a novel strain of methanogenic bacteria belonging to the genus Methanobacterium is used for the fermentation, by which methane is produced even in an atmosphere containing a certain level of oxygen.

It is another object of the present invention to provide a methane fermentation process which is feasible under relatively mild temperature conditions.

It is a further object of the present invention to provide an efficient manner of growing the novel strain of methanogenic bacteria thereby providing a seed of the bacteria for use as the methane fermentation.

The above objects can be achieved, according to the invention, by a methane fermentation process which comprises providing a seed of methanogenic bacteria belonging to the genus Methanobacterium and cultivating the seed in a fermenter containing at least a carbon source, a nitrogen source, inorganic salts and microorganisms constituting micro-flora of methane fermentation at a temperature of 25° to 45° C., said bacteria having a methanogenic activity over $8.7 \times 10^{-8}$ ml/cell·day in the stationary phase of growth, exhibiting the methanogenic activity even at a partial pressure of oxygen of 1/30 atm. and being allowed to live under an oxygen partial pressure up to 1/5 atm. The methane fermentation should be conducted under oxygen-free or anaerobic conditions though the fermentation may be effected at a certain level of oxygen partial pressure when using the bacteria of the above-mentioned type.

DETAILED DESCRIPTION AND EMBODIMENTS OF THE INVENTION

We have made extensive studies to discover methanogenic bacteria which have the high methanogenic activity in the stationary phase of growth and are resistant to oxygen. That is, a number of bacteria were screened from sediments in ponds and marshes and sludges from anaerobic digesters. As the result, a strain of mesophilic (25° C. to 40° C.) methanogenic bacteria was collected. This strain is called Methanobacterium sp. ST-23 and was deposited as FERM BP-44 at the Fermentation Research Institute Agency of Industrial Science and Technology of the Ministry of International Trade and Industry of Japan. A copy of "RECEIPT IN THE CASE OF AN ORIGINAL DEPOSIT" for this strain is incorporated herein. It is important to note that the bacteria useful in the present invention belong to the genus Methanobacterium and have a methanogenic activity over $8.7 \times 10^{-8}$ ml/cell·day in the stationary phase of growth, exhibiting the methanogenic activity even at a partial pressure of 1/30 atm. and being allowed to live under an oxygen partial pressure up to 1/50 atm.

This strain was isolated from a pond sediment as a dominant species and was found to live in the sludge at $10^8$–$10^9$ in number per ml of the sludge.

The strain readily reaches its stationary phase of growth when cultivated in a culture medium well known in the art at a temperature ranging from 25° to 45° C. For instance, the liquid culture of the present strain at 35° C. using a culture medium having a composition indicated in Table 1 results in a stationary phase of growth in about 7 days.

TABLE 1

| | | | |
|---|---|---|---|
| $KH_2PO_4$ | 0.021% | Biotin* | 0.4 µg/ml |
| $K_2HPO_4$ | 0.021% | Folic acid | 0.4 µg/ml |
| $(NH_4)_2SO_4$ | 0.021% | Pyridoxine | 2 µg/ml |
| NaCl | 0.042% | hydrochloride* | |

TABLE 1-continued

| | | | |
|---|---|---|---|
| $MgSO_4.7H_2O$ | 0.0084% | Thiamine hydrochloride* | 1 µg/ml |
| $CaCl_2.2H_2O$ | 0.015% | | |
| Resazurin sodium salt | 0.001% | Riboflavine* | 1 µg/ml |
| | | Nicotinic acid | 1 µg/ml |
| $ZnSO_4.7H_2O$ | 100 µg/ml | Calcium pantothenate | 1 µg/ml |
| $MnCl_2.4H_2O$ | 30 µg/ml | | |
| $H_3BO_3$ | 300 µg/ml | Vitamin $B_{12}$ | 0.02 µg/ml |
| $CoCl_2.6H_2O$ | 200 µg/ml | p-Aminobenzoic acid* | 1 µg/ml |
| $NiCl_2.6H_2O$ | 20 µg/ml | | |
| $Na_2MoO_4.2H_2O$ | 30 µg/ml | DL-Thioctic acid* | 1 µg/ml |
| $FeCl_3.nH_2O$ | 150 µg/ml | Cystein monohydrochloride monohydrate* | 0.025% |
| | | $Na_2S.9H_2O$* | 0.025% |
| | | $Na_2CO_3$* | 0.1% |

*These compounds are separately sterilized.

When the culture in which the bacteria had completely reached the stationary phase was used to determine the methanogenic activity using a substrate of hydrogen and carbon dioxide, the activity was found to be at least $8.7 \times 10^{-8}$ ml/day·bacterium. The cell counts were determined by the colony counting method. The analysis of the methane gas was carried out by gas chromatography. The above methanogenic activity corresponds to 13 m$^3$/day of $CH_4$ as calculated using the tank capacity of 1.5 m$^3$ in the afore-indicated process on the basis of $10^8$ bacteria/ml which are a lower limit of the concentration of the present bacteria in sludge. This is a very high methanogenic activity.

The resistance of the present bacteria to oxygen is described.

The following test was conducted: 50 ml of the medium of the composition indicated above was introduced into a 110 ml serum bottle with a head space of 60 ml, to which was added 1 ml of hydrogen sulfide and cysteine as a reducing agents serving to reduce oxygen therewith. Then, oxygen was added an amount ranging 0-12 ml to the head space, into which was further charged a mixed gas of 80% by volume of hydrogen and 20% by volume of carbon dioxide to a pressure 1.5 atms., followed by cultivating at 35° C. As a result, it was confirmed that the addition of oxygen up to 2 ml leads to formation of methane in small amounts (0.05 ml of $CH_4$/3 days) after three days. It was also confirmed by the plate assay that even after 14 days, the system did not undergo any contamination with other bacteria and the number of bacteria did not decrease when up to 12 ml of oxygen was added. The amount of oxygen of 12 ml in 60 ml of the head space is almost equal to the oxygen concentration in air, and thus the present strain can viably withstand a partial pressure of oxygen in air. In this connection, bacteria of *Methanobacterium mobile* have been reported to die out in the presence of oxygen in an amount not greater than an equivalent of reducing agent (Journal of Bacteriology, Vol. 95, Column 1943, 1968). Accordingly, the characteristics of the present strain greatly differ from those of these strains.

The present strain ST-23 has the following bacteriological properties. It will be noted that the culture was effected using a medium of Table 1 and a gas phase composition of 80% by volume of hydrogen and 20% by volume of carbon dioxide.

(1) Observations by Optical and Electronic Microscopes

The bacterium is a straight to slightly curved rod 0.3 microns in diameter and 1.3 to 3.3 microns in length with round ends. The bacterium undergoes a considerable unequivalent division and is occasionally in the form close to sphere. It is non-sporing, nonmotile, with no flagella and gram-negative.

(2) Surface Colonies

The bacteria are poor in growth with micro-colonies appearing 4 days after inoculation and forms colonies in 14 days having a maximum diameter of 0.7 to 1 mm. Young colonies are round, entire, and white to light yellow in color and old colonies are thinly, shallowly, radially wrinkled on the shallow surface thereof.

(3) Growth Conditions

The bacteria are mesophilic anaerobic bacteria growing in the vicinity of neutral pH range and utilize for growth hydrogen and carbon dioxide, or formates, or acetates. They withstand a partial pressure of oxygen up to 1/5 atms. and have the ability of producing methane under a partial pressure up to 1/30 atm. No acceleration of growth is found using peptone and amino acids and co-enzyme M. Yeast extract is found to slightly accelerate the growth. A soluble fraction of pond sediment does not contribute to the growth acceleration but the coculture with a certain type of bacteria results in a remarkable acceleration of growth.

(4) Others

The soluble fraction of homogenate of the present bacteria emits a bluish green fluorescence upon application of near ultraviolet rays.

The taxonomic position of the present strain is determined according to the Bargey's Manual of Determinative Bacteriology. In view of the fact that the bacteria are rod-shaped and capable of producing methane, they are believed to belong to the genus Methanobacterium and to be nearly related to *Methanobacterium formicicum* or *Methanobacterium mobile*. However, these related bacteria are different from the present bacteria in many respects including no utilizability of acetate. Accordingly, the present strain is considered to be a novel strain belonging to the genus Methanobacterium and a novel species name, *Methanobacterium kadomensis*, was given on the basis of the location of the sediment which is a screening source. As mentioned, this strain was deposited as FERM BP-44 at the Fermentation Research Institute Agency of Industrial Science and Technology of the Ministry of International Trade and Industry of Japan, which is one of international depositary authorities, based on the Budapest Treaty on the international recognition of the deposit of microorganisms for the purposes of patent procedure.

The strain obtained in the procedure as described before is used for methane fermentation by inoculating it in a fermenter which comprises inorganic salts, carbon sources, nitrogen sources and microorganisms constituting micro-flora of methane fermentation necessary for methane fermentation at a temperature ranging from (25° C.) to 45° C. By the term "microorganisms constituting micro-flora of methane fermentation" are meant microorganisms which serve to liquefy carbon sources and convert them into low molecular weight materials including hydrogen, carbon dioxide and the like which are utilizable by the bacteria for methane fermentation. The microorganisms constituting the micro-flora of methane fermentation can readily be obtained by thermally treating a sludge such as kitchen refuse at a temperature sufficient for killing methanogenic bacteria, say, about 70° C. for several minutes. As a matter of course, the methane fermentation can be carried out continuously or in a batchwise manner and under anaerobic conditions.

In the application of the present bacteria to the methane fermentation, it is necessary to cultivate and collect the bacteria in large amounts. As briefly mentioned, the bacteria can be cultivated under anaerobic and mesophilic conditions in the pH range of 6 to 8 and preferably in the vicinity of a pH of 7 using as a substrate hydrogen and carbon dioxide, or formate or acetate and as a culture medium at least nitrogen sources, inorganic salts and reducing agents. The nitrogen sources and inorganic salts are those ordinarily employed for this purpose as indicated in Table 1. The reducing agents are used for the following reason: the cultivation proceeds rapidly at an oxidation-reduction potential of about $-300$ mV and for this purpose, the reducing agents are used and when an atmosphere of a tank or fermenter is replaced by an inert gas, it is unavoidable that oxygen in the atmosphere remains in the tank and is removed by reduction with these reducing agents. Examples of the reducing agents include sulfur-containing materials such as hydrogen sulfide, cysteine and the like. In addition, other types of reducing agents such as trivalent titanium compounds may be used in combination with the sulfur-containing materials. An increasing amount of reducing agents such as sodium sulfide will cause the bacteria to be barely affected by oxygen but an excess of reducing agent impedes the growth of the methanogenic bacteria.

As described hereinbefore, the substrate for the culture is hydrogen and carbon dioxide, formates such as Na, K, Ca and Mg salts or acetates such as Na, K, Ca and Mg salts. Preferably, the mixture of hydrogen and carbon dioxide or a formate is used. Acetates are utilized only very slowly as will be understood thermodynamically. A combination of a formate and hydrogen may be used, in which case a high partial pressure of hydrogen impedes the growth of the bacteria. When hydrogen and carbon dioxide are used in combination as the substrate, the substrate composition is suitably composed of 80% by volume of hydrogen and 20% by volume of carbon dioxide as theoretical for the methane production. In this connection, however, at the initial stage of the cultivation, the mixed gas of hydrogen and carbon dioxide is favorably diluted with an inert gas such as nitrogen gas by which the growth of the bacteria is facilitated. The culture temperature is in the mesophilic range of 25° C. to 45° C. The pH of the medium is suitably near neutral though depending on the concentration of carbon dioxide in the gas phase. When a formate is used, the pH increases with a decrease of the formate utilized, so that the medium composition should be a buffer solution or should be invariably neutralized during the course of the cultivation. In Table 1, vitamins are used but instead, vitamin sources such as yeast extracts may be used.

The cultivated bacteria can readily be collected by any known techniques such as centrifugal separation, cosedimentation and the like for use as a seed for the methane fermentation. Alternatively, they may be admixed with other microorganisms useful for the methane fermentation and applied to the methane fermentation as they are.

Although the methanogenic bacteria used in the practice of the invention can be cultivated to give a seed of the bacteria in a manner as described hereinabove, their growth by pure cultivation is relatively poor and is at such a level that the optical density at 660 nm is 0.01 and the concentration of bacteria is $10^6$/ml.

In order to improve the growth efficiency, we have made an investigation to obtain microorganisms showing the accelerating action on growth of the methanogenic strain and found that a strain called YN-28 is effective for this purpose. The strain YN-28 exhibits the highest growth-accelerating effect among 935 strains isolated by the random screening and its effect was confirmed by the following experiment.

300 ml of a medium having the composition indicated in Table 2 was placed in a 500 ml flask.

TABLE 2

| Trypticase (BBL) | 0.05% | Cystein hydrochloride* | 0.025% |
|---|---|---|---|
| Yeast extract | 0.05% | $Na_2S.9H_2O$* | 0.025% |
| $KH_2PO_4$ | 0.021% | Sodium Resazurin | 0.001% |
| $K_2HPO_4$ | 0.021% | $Na_2CO_3$ | 0.4% |
| $(NH_4)_2SO_4$ | 0.021% | Nicotinic acid* | 20 µg/ml |
| NaCl | 0.042% | Vitamin $B_{12}$* | 10 µg/ml |
| $MgSO_4.7H_2O$ | 0.0084% | Thiamine hydrochloride* | 5.6 µg/ml |
| $CaCl_2.2H_2O$ | 0.015% | Paraminobenzoic acid* | 5 µg/ml |
| $ZnSO_4.7H_2O$ | 100 µg/ml | | |
| $MgCl_2.4H_2O$ | 30 µg/ml | | |
| $H_3BO_3$ | 300 µg/ml | | |
| $CoCl_2.6H_2O$ | 200 µg/ml | | |
| $NiCl_2.2H_2O$ | 20 µg/ml | | |
| $Na_2MoO_4.2H_2O$ | 30 µg/ml | | |
| $FeCl_2.nH_2O$ | 150 µg/ml | | |

*These compounds are separately sterilized.

Then, an acetyl cellulose dialysis sac was suspended in the medium, after which the strain YN-28 was inoculated into the inner liquid and the strain ST-23 was inoculated into the outer liquid. The flask was provided with a cotton stopper and the bacteria were cultivated at a temperature of 35° C. in a gas phase of 90% nitrogen, 5% hydrogen and 5% carbon dioxide. Two days after the cultivation, the optical density at 660 nm of the outer liquid reached 0.5. It was confirmed by the microscopic observation that both the bacteria did not mix through the dialysis sac. In contrast, with the control test where no strain YN-28 was inoculated into the inner liquid, the optical density at 660 nm after the seventh day was found to be 0.01. That is, the YN-28 showed a high growth-accelerating effect on the methanogenic strain ST-23.

The bacteriological properties of the strain YN-28 which is cultivated in a PY medium (containing each 1% of pepton and yeat extract) used as a fundamental medium are as follows.

(1) Microscopic Observation

This strain is a rod 1 to 1.2 microns in diameter and 3 to 15 microns in length and is found singly or in short chains. It is motile, and its spore position is central to subterminal. The spores are oval and the bacteria are gram-positive.

(2) Surface Colonies

The colonies are round, entire and convex at the initial stage of cultivation and 3 days after the cultivation, they are 6 to 8 mm in diameter and become circular with irregular margins and are nearly in the form of a trapezoid in longitudinal section. They are yellowish white in color and have a glossy surface. The turbidity varies depending on the degree of formation of spores and their growth is good.

(3) Physiological Properties (a) The bacteria are positive with respect to the gelatin hydrolytic activity, casein hydrolytic activity, lecitinase activity, and hydrosulfide releasing activity.

(b) Negative with respect to lipase activity and urease activity.

(c) Capable of forming acids from fructose, glucose and maltose.

(d) Weakly positive with respect to the ability of forming acids from mannose, ribose and xylose.

(e) Negative with respect to formation of acids from esculine, lactose, mannitol, melibiose, salicin, sucrose and starch.

(f) Positive with respect to hydrolysis of esculine and negative to the hydrolysis of starch.

(4) Others

The liquid culture gives a viscous cell precipitate.

When the taxonomical position of the strain YN-28 is determined according to the Bergey's Manual of Determinative Bacteriology, the eighth edition, it is apparent that the strain belongs to the genus Clostridium. More particularly, the strain is akin to *Clostridium bifermentans* and no basis of proving it as other species is found, so that it is proper to consider this strain as one of strains of *Clostridium bifermentans*.

Similar to the strain ST-23, it was deposited at the Fermentation Research Institute Agency of Industrial Science and Technology as FERM BP- 141.

As described hereinbefore, the strain ST-23 can be cultivated and collected in large amounts by anaerobically cultivating the strain in a medium containing at least nitrogen sources, minerals or inorganic salts and reducing agents using as a substrate for growth hydrogen and carbon dioxide, or formates or acetates in the vicinity of a pH of 7 in a mesophilic range.

The coculture of the strains ST-23 and YN-28 is effected in a manner similar to the culture of ordinary anaerobic bacteria. For instance, the coculture is carried out using carbon sources, nitrogen sources, minerals, reducing agents and vitamins as indicated in Table 2. Vitamins are not necessarily needed. Because reducers are formed on decomposition of organic matters with the strain YN-28, addition of reducing agents is not necessarily required. In this connection, sodium sulfide and cysteine are used as sulfur sources in Table 2. Addition of sugars facilitates the growth of the strain YN-28 but they are converted into acids to lower the pH of medium, thus inhibiting the growth of the strain ST-23. Accordingly, use of sugars should favorably be avoided. The pH of medium is about 7 and the temperature is optimumly in the mesophilic range of 35° C. to 45° C. The partial pressure of oxygen in the gas phase is in the range up to 1/30 atm. where the strain ST-23 grows. Use of a mixed gas of hydrogen and carbon dioxide as the gas phase is more effective in growth of the strain ST-23.

The cultivated cell mass of methanogenic bacteria may be collected by known techniques such as centrifugation, cosedimentation and the like or may be mixed with microorganisms constituting micro-flora of methane fermentation and applied to the methane fermentation of the present invention. The microorganisms constituting micro-flora of methane fermentation may be either pure or mixed microorganisms.

The present invention is particularly described by way of the following examples, which should not be constructed as limiting the present invention thereto.

EXAMPLE 1

A liquid medium having the composition of Table 1 was placed in a 700 ml serum bottle in an amount of 500 ml and autoclaved at 120° C. for 10 minutes, but vitamins, sodium carbonate, cystein hydrochloride and sodium sulfide were separately subjected to filter sterilization and then combined with the sterilized liquid medium obtained after completion of the autoclave treatment. The bottle was sealed tightly with a butyl rubber stopper and covered with an aluminium cap. Then, the gas phase in the head space was replaced by a mixed gas of 80% by volume of hydrogen and 20% by volume of carbon dioxide by the use of an injection needle up to a level of 1.5 atms. Further, the liquid culture of the strain ST-23 was injected through the rubber stopper at a rate of 1% of the total composition and cultured at 35° C. During the course of the culture, the mixed gas was added every other day. Ten days after the culture, the turbidity measured at a wavelength of 660 nm was found to be 0.01 and the concentration of cells determined by the colony counting method was $10^6$/ml. From this culture, there were obtained 200 mg of wet cells by the centrifugation under conditions of 8000 G and 10 minutes.

EXAMPLE 2

The strain ST-23 was cultivated under the same conditions as in Example 1. The cell mass collected by the centrifugation from four bottles was used to effect the following test. Microorganisms other than methanogenic bacteria constituting micro-flora of methane fermentation were obtained by thermally treating a sludge in the methane fermenter, which was run using kitchen refuse as a starting material, at a temperature of 70° C. for 20 minutes, thus losing methanogenic activity.

A starting material for fermentation had a composition of a pH of 7 indicated in Table 3 below.

TABLE 3

| | |
|---|---|
| $K_2HPO_4$ | 0.3% |
| $KH_2PO_4$ | 0.2% |
| $(NH_4)_2CO_3$ | 0.5% |
| $Na_2CO_3$ | 0.3% |
| $FeCl_3.6H_2O$ | 0.1% |
| Corn steep liquor | 0.5% |
| Glucose | 12% |

18 ml of the total of the strain ST-23 and the thermally treated sludge was placed in a 200 ml injection syringe, from which the air was withdrawn. Two milliliters of the starting material was charged through a tip portion or the Luer lock portion of the syringe and the tip was covered with a rubber cap. Thereafter, 2 ml of the fermented liquor was withdrawn from the injection syringe every day while adding 2 ml of a fresh starting material.

The generation of fermentation gas was read out from the scale of the injection syringe and the gas was discharged through the tip portion.

The results of the test are as shown in Table 4. It will be noted that the methane concentration in the gas generated at the fourth day of the test was found to be 53%.

TABLE 4

| Days After Commencement of the Culture | Amount of Generated Gas |
|---|---|
| 1 | 145 ml |
| 2 | 210 |
| 3 | 195 |
| 4 | 200 |

EXAMPLE 3

300 ml of the culture medium indicated in Table 2 was charged into a 500 ml flask, in which the strains ST-23 and YN-28 were cocultured in an atmosphere of 90% by volume of nitrogen, 5% by volume of hydrogen and 5% by volume of carbon dioxide. The culture medium was sampled at certain intervals of time and the concentration of cells in the culture medium was determined by the colony counting method with the results shown in Table 5.

TABLE 5

| Cultivation Time (hours) | ST-23 | YN-28 |
|---|---|---|
| 0 | $10^5$/ml | $4.5 \times 10^3$/ml |
| 24 | $4 \times 10^7$/ml | $3.2 \times 10^5$/ml |
| 48 | $8.2 \times 10^7$/ml | $3.4 \times 10^5$/ml |
| 72 | $1.1 \times 10^8$/ml | $3.0 \times 10^5$/ml |

As will be understood from the foregoing description, the present invention provides an efficient methane fermentation process using methanogenic bacteria which are high in methanogenic efficiency and resistant to oxygen. These methanogenic bacteria can efficiently be grown or cultivated to give a seed for the methane fermentation.

What is claimed is:

1. A fermentation process comprising:
   (a) inoculating a bacteria strain of the genus Methanobacterium in a fermentation media which comprises at least inorganic salts, carbon sources, nitrogen sources and micro-flora of methane fermentation which are capable of liquifying the carbon sources and convert the carbon sources to low molecular weight materials which are utilized by the bacteria strain for methane fermentation, said bacteria strain having all the identifying characteristics of strain ST-23 (FERM BR-44),
   (b) maintaining the fermentation media at a temperature of 25° to 45° C. whereby methane is produced, and
   (c) collecting the produced methane from the fermentation media.

2. A fermentation process according to claim 1 wherein the bacteria strain of the genus Methanobacterium is strain ST-23 (FERM BR-44).

3. The methane fermentation process according to claim 1 wherein the fermentation media is kept at a temperature of 35° to 40° C.

4. The methane fermentation process according to claim 1 wherein the bacteria strain is a seed bacteria which is prepared by anaerobically cultivating cells of strain ST-23 in a culture medium comprising at least nitrogen sources, inorganic salts, reducing agents and at least one substrate selected from the group consisting of a mixed gas of hydrogen and carbon dioxide, a formate and an acetate in a mesophilic range of 25° to 40° C., and centrifugally separating the cultivated cells.

5. The methane fermentation process according to claim 4, wherein said substrate is mixed gas of hydrogen and carbon dioxide.

6. The methane fermentation process according to claim 4, wherein said mixed gas is composed of 80% by volume of hydrogen and 20% by volume of carbon dioxide and the pH of the culture medium is kept in the range of 6 to 8.

7. The methane fermentation process according to claim 4, wherein said substrate is formate and said culture medium is kept in the range of 6 to 8 in pH.

8. The methane fermentation process according to claim 4, wherein said bacteria strain is cocultured with a strain having all the identifying characteristics of bacteria strain YN-28 of the species *Clostridium bifermentans*.

9. The methane fermentation process according to claim 8, wherein said strain is strain YN-28 of the species *Clostridium bifermentans*.

10. The methane fermentation process according to claim 9, wherein the coculture is effected in a pH range of from 6 to 8.

* * * * *